(12) United States Patent
Berg

(10) Patent No.: US 8,466,184 B2
(45) Date of Patent: Jun. 18, 2013

(54) BIOCIDE

(75) Inventor: Carsten Berg, Borre (DK)

(73) Assignee: Titan Chemicals Limited, Tortola (VG)

( * ) Notice: Subject to any disclaimer, the term of this patent is extended or adjusted under 35 U.S.C. 154(b) by 0 days.

(21) Appl. No.: 13/282,508

(22) Filed: Oct. 27, 2011

(65) Prior Publication Data

US 2013/0109727 A1    May 2, 2013

(51) Int. Cl.
*A01N 43/80* (2006.01)
(52) U.S. Cl.
USPC ............................................ 514/373

(58) Field of Classification Search
USPC ............................................... 514/373
See application file for complete search history.

(56) References Cited

U.S. PATENT DOCUMENTS 3,970,755 A    7/1976    Gazzard et al.

FOREIGN PATENT DOCUMENTS

WO    02/14293    2/2002

*Primary Examiner* — San-Ming Hui
(74) *Attorney, Agent, or Firm* — Clark & Brody

(57) ABSTRACT

Aqueous solutions of the tetramethylammonium salt of 1,2-benzothiazolone stable below 0° C.

5 Claims, No Drawings

BIOCIDE

This invention relates to biocides. More especially the invention relates to the tetramethylammonium salt of 1,2-benzisothiazolin-3-one. 1,2-benzisothiazolin-3-one sometimes referred to hereinafter as BIT is a well-known biocide which is used inter alia in paint and in water cooling systems. BIT itself is not very water soluble. While it can be used either as a suspension or as a solution in an organic solvent neither option is especially favourable. In the case of suspensions settling can occur leading to difficulties in dosage. The problems of using solutions based on volatile organic solvents are well known.

It has been proposed to use salts of BIT. These salts are water soluble and this overcomes the problems of using suspensions and organic solutions and water solutions of salts of BIT for example the sodium salt are useful in warm environments. Solutions of BIT salts crystallise at comparatively high temperatures and so water solutions of them are not useful at low temperatures unless stabilised by the addition of organic materials such as glycol.

Many salts of BIT are known. For example U.S. Pat. No. 3,970,755 describes a range of quaternary ammonium salts of BIT. WO 02 14 293 also describes a number of salts of BIT. Furthermore WO 02 14 293 measures the freezing point of solutions of the salts it describes. In this document the minimum freezing point of a water solution of a range salts of BIT was reported. Among these results is reported data for the tetramethylammonium salt of BIT hereinafter referred to as "tetramethylammonium BIT". The lowest freezing point water solution was found to contain 59 wt % tetramethylammonium BIT which corresponds to 40 wt % BIT and have a freezing point of 3° C. after storage for 24 hours and seeding with solid tetramethylammonium BIT.

It has known been very surprisingly found that the reported freezing point is not correct and that water solutions of tetramethylammonium BIT are stable at much lower temperatures than hitherto realised.

According to the invention there is therefore provided a composition consisting essentially of water and the tetramethylammonium salt of 1,2-benzisothiazolin-3-one having a freezing point of less than about 0° C., such as less than about −1° C. for example less than about −3° C., about −5° C., about −10° C., about −15° C., about −20° C., about −25° C. or −30° C. As used herein the expression "freezing point" means that the composition is fluid after 24 hours and seeded with solid tetramethylammonium salt of 1,2-benzisothiazolin-3-one.

If even lower freezing points are required than are achievable with only water it is possible to add a water-miscible organic solvent. Examples of such water-miscible organic solvents can include aliphatic alcohols having 1 to 4 carbon atoms such as ethanol and isopropanol, glycols such as ethylene glycol, diethylene glycol, 1,2-propylene glycol, dipropylene glycol and tripropylene glycol, glycol ethers such as butyl glycol and butyl digylcol, glycol esters such as 2,2,4-trimethylpentanediol monoisobutyrate, polyethylene glycol, polypropylene glycol, N,N-dimethylformamide and mixtures thereof. Preferably less than about 5 wt % water-miscible organic solvent is used but higher concentration for example up to about 10 wt %, 15 wt % or about 20 wt % can be used if necessary.

The pH of the composition is generally neutral or slightly alkaline for example about 8 to about 10.

The biocide composition of the invention can also contain other customary constituents known as additives to those skilled in the art in the field of biocides. These are, e.g., thickening agents, defoaming agents, substances to adjust the pH value, perfumes, dispersing agents, and coloring substances.

The biocide composition of the invention can be used in many different fields. It is suitable, for example, for use in paints, plasters, lignosulfonates, chalk suspensions, adhesives, photochemicals, casein-containing products, starch-containing products, bituminous emulsions, surfactant solutions, motor fuels, cleaning agents, cosmetic products, water circulating systems, polymer dispersions, and cooling lubricants, against attack by, for example, bacteria, filamentous fungi, yeasts, and algae.

In practice, the biocide composition can be used either as a ready-to-use mixture or by adding the biocides and the remaining components of the composition separately to the substance to be preserved.

As used herein the expression "composition consisting essentially of water and the tetramethylammonium salt of 1,2-benzisothiazolin-3-one" may mean a solution containing not more than about 5 wt % of ingredients other than water and the tetramethylammonium salt of 1,2-benzisothiazolin-3-one.

Tetramethylammonium BIT can be prepared as described in WO 02 14 293 by reacting tetramethylammonium hydroxide solution with BIT. While solid tetramethylammonium pentahydrate is known it is very expensive and practically it is necessary to use the much cheaper water solution. This is typically available as 5 to 25 wt % solutions. Reaction of 25 wt % tetramethylammonium hydroxide with BIT gives rise to a 39 wt % solution containing the equivalent of 26 wt % BIT. If more concentrated solutions (up to about 40 wt % BIT) are required water can be evaporated from the solution. The pure compound can be obtained by dehydration under reduced pressure. If more dilute solutions are required then more dilute tetramethylammonium hydroxide can be used or the prepared solution can be diluted.

In general the solution should have a BIT content of more than about 5 wt %, such as about 10 wt % or about 15 wt %. Commercial solutions of sodium BIT contain about 20 wt % BIT and so concentrations of this order are very useful since no reformulation is required. More concentrated solutions such as about 25 wt % or about 30 wt % or about 35 wt % or about 40 wt % such as 42.6 wt % or 43 wt % may also be useful.

EXAMPLE 1

Production of Tetramethylammonium BIT

To a solution of water of tetramethylammonium hydroxide (25%, 101.6 g) was added BIT (water content 20% dry purity 98%, 54.6 g) with agitation to pH 9.58 to give a solution of the title compound in water 39 wt % corresponding to 25 wt % BIT. Water was evaporated to give more concentrated solutions and the pure material was obtained in quantitative yield.

$^1$H NMR (250 MHz, DMSO) d: 3.14 (s, 12H, 4CH$_3$), 7.11 (t, 1H J=7.0 Hz, ArH), 7.25 (t, 1H, 1=7.0 Hz, ArH), 7.57 (d, 1H J=7.8 Hz ArH), 7.64 (d, 1H J=7.6 Hz ArH)

EXAMPLE 2

Measuring Stability of Water Solutions

A series of solutions of tetramethylammonium BIT in distilled water were prepared. In series of experiments the temperature at which the solution remained fluid after 24 hours and seeding with a seed crystal of tetramethylammonium BIT was measured. The results are reported in Table 1

| % BIT concn | Temp (° C.) |
|---|---|
| 45 | 5 |
| 42.6 | −10 |
| 39.3 | −32 |
| 35.6 | −20 |
| 30.4 | −13 |
| 25.3 | −8 |
| 20.3 | −5 |

It will therefore be apparent that a wide range of water solutions of BIT remain fluid at low temperatures.

The invention claimed is:

1. A composition consisting essentially of water and the tetramethylammonium salt of 1,2-benzisothiazolin-3-one having a freezing point less than 0° C. other than a composition consisting of 59 wt % of the tetramethylammonium salt of 1,2-benzisothiazolin-3-one corresponding to 40 wt % benzisothiazolin-3-one with the balance being water.

2. The composition of claim 1 wherein the content of the tetramethylammonium salt of 1,2-benzisothiazolin-3-one calculated as 1,2-benzisothiazolin-3-one is in the range about 10 wt % to less than about 40 wt %.

3. The use of the tetramethylammonium salt of 1,2-benzothiazolone in producing an aqueous biocidal solution having a freezing point less than 0° C.

4. A method of killing a microorganism comprising contacting the microorganism with the composition of claim 1.

5. The composition of claim 1 wherein the content of the tetramethylammonium salt of 1,2-benzisothiazolin-3-one calculated as 1,2-benzisothiazolin-3-one is in the range of greater than about 40 wt % to about 43 wt %.

* * * * *